United States Patent
Buttle et al.

(10) Patent No.: US 7,053,606 B2
(45) Date of Patent: May 30, 2006

(54) MEASUREMENT OF RESIDUAL AND THERMALLY-INDUCED STRESS IN A RAIL

(75) Inventors: David John Buttle, Wantage (GB); William Dalzell, Winchester (GB); Peter John Thayer, Oxford (GB)

(73) Assignee: AEA Technology plc, Didcot (GB)

( * ) Notice: Subject to any disclaimer, the term of this patent is extended or adjusted under 35 U.S.C. 154(b) by 0 days.

(21) Appl. No.: 10/535,211

(22) PCT Filed: Feb. 13, 2004

(86) PCT No.: PCT/GB2004/000556

§ 371 (c)(1),
(2), (4) Date: May 17, 2005

(87) PCT Pub. No.: WO2004/077003

PCT Pub. Date: Sep. 10, 2004

(65) Prior Publication Data

US 2006/0028205 A1 Feb. 9, 2006

(30) Foreign Application Priority Data

Feb. 25, 2003 (GB) ................................ 0304192.8

(51) Int. Cl.
*B61K 9/10* (2006.01)
*G01N 27/82* (2006.01)
(52) U.S. Cl. .................. 324/217; 324/209; 73/779
(58) Field of Classification Search ............... 324/209, 324/217; 73/779, 766, 862.69
See application file for complete search history.

(56) References Cited

U.S. PATENT DOCUMENTS

| | | | | |
|---|---|---|---|---|
| 4,279,163 A | * | 7/1981 | Takekoshi et al. | ............. 73/761 |
| 5,828,211 A | | 10/1998 | Scruby | ........................ 324/209 |
| 5,992,241 A | | 11/1999 | Posgay | ......................... 73/779 |
| 6,657,429 B1 | * | 12/2003 | Goldfine et al. | ............. 324/232 |
| 6,850,055 B1 | * | 2/2005 | Buttle | ......................... 324/209 |
| 2003/0173958 A1 | * | 9/2003 | Goldfine et al. | ............. 324/209 |

FOREIGN PATENT DOCUMENTS

| | | |
|---|---|---|
| EP | 0703439 | 3/1996 |
| GB | 2278450 | 11/1994 |
| JP | 58 216924 | 12/1983 |
| WO | 89/01613 | 2/1989 |
| WO | 03/034054 | 4/2003 |

* cited by examiner

*Primary Examiner*—Jay M. Patidar
(74) *Attorney, Agent, or Firm*—William H. Holt

(57) ABSTRACT

In a railway line, thermally-induced stresses are a factor for both rail breaks and rail buckling. These stresses are in the longitudinal direction. A nondestructive measuring technique enables the residual stress in a rail to be determined, and hence the thermally-induced stress. An electromagnetic probe is used to measure the stresses in the rail web in the vertical direction, and in the direction parallel to the longitudinal axis. The residual stress in the longitudinal direction can be deduced from the measured stress in the vertical direction; hence the thermally-induced stress can be determined.

8 Claims, 3 Drawing Sheets

MEASUREMENT OF RESIDUAL AND THERMALLY-INDUCED STRESS IN A RAIL

This invention relates to a method and apparatus for determining residual stress in a ferromagnetic object such as a rail of a railway line, preferably using an electromagnetic probe.

The stresses in structures such as rails, bridges and pipelines, complex mechanisms such as vehicles and machinery, or simple devices such as struts, cables or bearings arise from various causes including changes of temperature, and the loads and pressures due to use. There may also be residual stresses arising from the fabrication of the structure or device, and any bending that the structure or device was subjected to during construction; the residual stresses arising from fabrication will also be affected by any stress-relieving heat treatment. A way of measuring stress in a steel plate is described in U.S. Pat. No. 5,828,211 (GB 2 278 450), this method using a probe containing an electromagnetic core to generate an alternating magnetic field in the plate, and then combining measurements from two sensors, one being a measure of stress-induced magnetic anisotropy (SMA), and the other being a measure of directional effective permeability (DEP). The probe is gradually turned around so the magnetic field has a plurality of different orientations in the plate, and these measurements are taken at each such orientation. The probe enables the stress to be measured near the surface, the depth of penetration depending upon the frequency.

In the case of railway lines, thermally-induced stresses are a contributing factor for both rail breaks (when the rail temperature falls, for example in winter), and for rail buckling (when the rail temperature rises, for example in summer). Traditionally in continuous-welded rail these problems are minimised by initially installing the rail in a state of tension, such that the thermal stresses would become zero if the rail temperature were to rise to a "stress-free temperature" which is selected such that in practice the thermal stresses do not reach excessive values. It would be desirable to be able to monitor the thermally-induced stresses in a rail, but this is no simple matter. As a rule, stress measurement techniques measure the total stress, which is the sum of the thermally-induced stress and the residual stress (as tensors); to determine the thermal stress it is therefore necessary to also ascertain the residual stress. This can be measured by measurements on a rail that is unconstrained, for example by cutting out a section of rail, but a nondestructive measurement technique would be desirable. (In this specification the term thermal stress or thermally-induced stress refers to the difference between the total stress and the residual stress.)

It will also be appreciated that accurate measurement of rail temperature is also very difficult to achieve, because of varying environmental conditions along a length of rail and because of the comparatively poor thermal conductivity of rail steel; an uncertainty in the mean temperature of any less than about +/−2° C. would be difficult to achieve. Temperature measurements in sunshine are likely to be even harder.

According to the present invention there is provided a method for determining the residual stress and the thermally-induced stress in a rail, the method comprising measuring the stresses in part of the rail remote from the railhead in a direction perpendicular to the longitudinal axis of the rail, and in a direction parallel to the longitudinal axis, determining from the stress in the perpendicular direction an estimate of the residual stress in the parallel direction, and hence by comparing the measured stress in the parallel direction to the estimated residual stress in the parallel direction determining the thermally-induced stress.

It has been discovered that residual stresses in rails vary from rail to rail, and through the life of a rail. However the lifetime variation can be minimised by considering stresses in regions remote from the railhead, that is to say in the web or possibly the foot of the rail. The residual stresses in both the parallel and perpendicular directions are principally caused by the straightening which is the final stage of manufacture of the rail, and consequently can be related to each other. In the web, for example, the residual stresses are typically compressive, in the region 120 to 220 MPa in the parallel direction, and 50 to 100 MPa in the perpendicular (vertical) direction. It should be appreciated that the variations in thermally-induced stress in the parallel direction in a straight track are only about 2.4 MPa/° C., so that variations in the residual longitudinal stress arising from the manufacturing process of say 50 MPa are generally much larger than the thermally-induced stresses.

In one embodiment of the invention the stress in the perpendicular direction is correlated with the residual stress in the parallel direction; in an alternative embodiment, the stress in the perpendicular direction is measured at different depths, and its variation with depth is correlated with the residual stress in the parallel direction. This alternative approach does not require absolute measurements of stress in the vertical direction, but only the difference in stress for different depths, and this may be desirable.

Preferably the stress is measured using an electromagnetic probe. In the preferred stress-measurement method the probe comprises an electromagnet means, means to generate an alternating magnetic field in the electromagnet means and consequently in the rail, and a magnetic sensor arranged to sense a magnetic field due to the electromagnet means; and the method comprises resolving signals from the magnetic sensor into an in-phase component and a quadrature component; mapping the in-phase and quadrature components directly into stress and lift-off components; and deducing the stress from the stress component so determined.

The mapping requires a preliminary calibration, with a specimen of the material, to determine how the in-phase and quadrature components of the signal vary with lift-off (at a constant stress) and vary with stress (at a constant lift-off), and deducing from the calibration measurements the applicable mapping for any stress and any lift-off. The mapping may be represented in the impedance plane (i.e. on a graph of quadrature component against in-phase component) as two sets of contours representing signal variation with lift-off (for different values of stress) and signal variation with stress (for different values of lift-off), the contours of both sets being curved. The contours of one set intersect the contours of the other set at non-orthogonal angles. Surprisingly it has been found that the angles at which the constant lift-off contours intersect any one contour of constant stress are all the same. Hence measurements taken along a few contours of each set enable the positions of the other contours of each set to be determined. This method of interpreting the signals and distinguishing between stress and lift-off is described in detail in WO 03/034054.

Surprisingly this simple mapping has been found to give an accurate representation of the variation of the signals with material property (e.g. stress), and provides a simple way to distinguish these variations from variations arising from lift-off or other geometrical variations such as surface texture or curvature.

Preferably the electromagnet means comprises an electromagnetic core and two spaced apart electromagnetic poles, and the magnetic sensor is preferably arranged to sense the reluctance (or flux-linkage) of that part of the magnetic circuit between the poles of the electromagnet means. It is also desirable to arrange for such measurements to be taken with a plurality of different orientations of the magnetic field, at a single location on the object. This may be achieved using a single probe that is rotated at that location, measurements being taken with different orientations of the probe. The sensor provides a measure of the permeability of the material through which the flux passes between the poles; the corresponding measurements at different probe orientations at a location on the object hence indicate the effective permeability in different directions.

The probe may also include a second magnetic sensor between the two poles and arranged to sense magnetic flux density perpendicular to the direction of the free space magnetic field between the poles. This second sensor would detect no signal if the material were exactly isotropic; however stress induces anisotropy into the magnetic properties of the material, and so the signals received by the second sensor (or flux-rotation sensor) are a measure of this stress-induced magnetic anisotropy. The variations in the flux rotation signals at different probe orientations, at a location on the object, enable the directions of the principal stress axes to be accurately determined. The flux rotation signals can also be related to the stress.

The probe may also include a third magnetic sensor (a flux-leakage sensor) between the poles arranged to sense magnetic flux density parallel to the free space magnetic field. This third sensor detects flux leakage which is influenced by changes in material properties, lift-off, and cracks. As with the flux-linkage sensor, measurements at a location are preferably made at different probe orientations.

The reluctance (or flux-linkage) signal from the probe is preferably backed-off, i.e. processed by first subtracting a signal equal to the signal from that sensor with the probe adjacent to a stress-free location. The backed-off signal is then amplified so the small changes due to stress are easier to detect. This backing off is performed after resolving into in-phase and quadrature components but before correcting for lift-off, for example by the mapping described above. Preferably the signals from the probe are digitized initially, and the backing-off and the lift-off correction are performed by analysis of the digital signals.

Generally, the more different probe orientations are used for taking measurements the more accurate the determination of stress levels can be. The measurements at different probe orientations at a particular location would usually be obtained by rotating the probe, but alternatively might be obtained using an array of probes of different orientations that are successively moved to that location. It will be appreciated that measurements of stress at different depths below the surface, where this is required, may be achieved by generating the alternating magnetic field with different frequencies.

The invention will now be further and more particularly described, by way of example only, and with reference to the accompanying drawings, in which.

Figure 1:
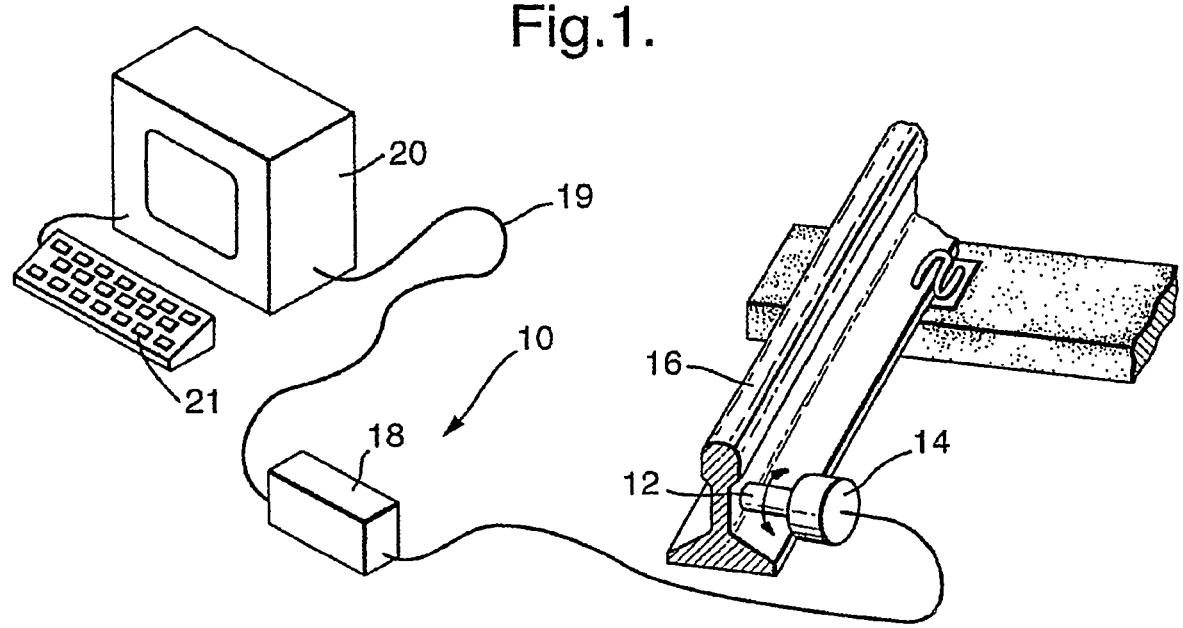
FIG. 1 shows a diagrammatic view of an apparatus for measuring stress.

Referring to FIG. 1, a stress measuring apparatus 10 includes a sensor probe 12 comprising sensors for flux-linkage, flux-rotation and flux-leakage, the probe 12 being attached to an electric motor 14 which can be held by an operator, so the motor 14 can turn the probe 12 with one end adjacent to a surface of a steel object 16 (the web of a rail in this case) in which the stresses are to be determined. The sensor probe 12 and motor 14 are connected by a 2 m long umbilical cable 17 to a signal conditioning/probe driver unit 18. The unit 18 is connected by a long umbilical cable 19 (which may for example be up to 300 m long) to an interface unit within a microcomputer 20, which has a keyboard 21. Operation of the apparatus 10 is controlled by software in the microcomputer 20.

Figure 2:
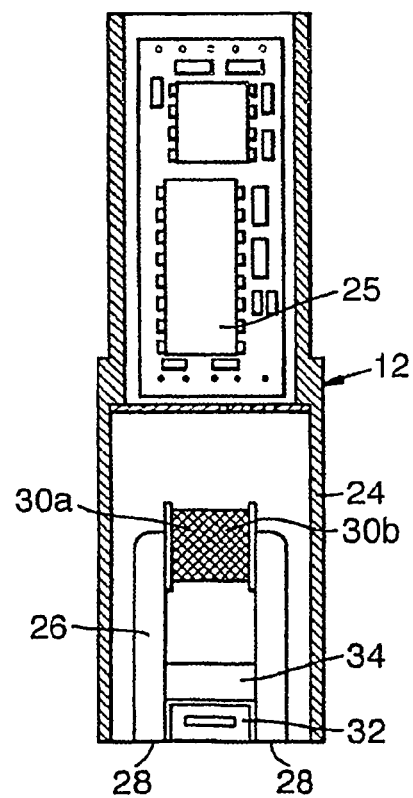
FIG. 2 shows a longitudinal sectional view of a probe for use in the apparatus of FIG. 1.

Referring now to FIG. 2, the probe 12 is shown detached from the motor 14, in longitudinal section although with the internal components shown in elevation (the connecting wires within the probe 12 are not shown).

The probe 12 comprises a cylindrical brass casing 24 of external diameter 16.5 mm and of overall height 60 mm, the upper half being of reduced diameter whereby the probe 12 is attached to the motor 14. The upper half of the casing 24 encloses a head amplifier 25. The lower half encloses a U-core 26 of laminated mu-metal (a high permeability nickel/iron/copper alloy) whose poles 28 are separated by a gap 7.5 mm wide, and are each of width 2.5 mm, and of thickness 10 mm (out of the plane of the figure). The poles 28 are in the plane of the lower end of the casing 24, which is open. Around the upper end of the U-core 26 is a former on which are wound two superimposed coils 30. One coil 30a (which has 200 turns) is supplied with the sinusoidal drive current from the unit 18; the other coil 30b (which has 70 turns) provides flux linkage signals.

Between the two poles 28 is a former on which is wound a 1670-turn rectangular coil 32, about 4 mm high and 6 mm wide, and 6 mm-square as seen from below, the windings lying parallel to the plane of the figure so the longitudinal axis of the coil 32 is perpendicular to the line between the centres of the poles 28. The coil 32 is supported by a support plate 34 fixed between the arms of the U-core 26 so the lower face of the coil 32 is in the plane of the poles 28. The coil 32 provides the flux-rotation signals. If a flux-leakage signal is required, a coil may be wound on the same former but with windings perpendicular to the plane of the figure. All the signals are amplified by the head amplifier 25 before transmission to the unit 18.

In operation of the system 10, the motor 14 is supported so the lower end of the probe 12 is adjacent to the surface of a steel object and the longitudinal axis of the probe 12 is normal to the surface. An alternating current of the desired frequency and amplitude is supplied to the drive coil 30a, so the magnetic field in the object 16 oscillates about zero with an amplitude much less than saturation. To set up the system 10, measurements are first made using an object of the same type of steel as the rail 16 but in which the stresses are negligible. The in-phase and quadrature components of the flux linkage signal (i.e. the component in phase with the drive current, and the component differing in phase by 90°) received by the microcomputer 20 are each backed off to zero, and the backing off values are then fixed. During all subsequent measurements the flux linkage components are backed off by these same amounts (i.e. subtracting a signal equal to the component observed at a stress-free location).

Stress measurements can be taken by placing the probe 12 adjacent to the web of the rail 16. The orientation of the line joining the centres of the poles 28 (referred to as the orientation of the probe 12) is noted relative to a fixed direction on the surface. The motor 14 is then energized to rotate the probe 12, for example in a step-wise fashion 10° at a time through a total angle of 360°. At each orientation of the probe 12 all the signals are measured.

It will be appreciated that the procedure of the invention is applicable with many different probes. The probe 12 might for example be modified by using a U-core 26 of a different material such as silicon iron (which can provide higher magnetic fields), or indeed the drive coil might be air-cored. The probe might be of a different shape or size; probes ranging in size between about 3 mm and 75 mm have been used for different purposes. In particular, for measurements on rails, a probe of diameter in the range 20 mm to 40 mm, e.g. 30 mm, would be suitable.

The flux rotation signals vary sinusoidally with probe orientation, so the orientation at which they have their maxima and minima can be determined. The directions midway between these two orientations are the directions of the principal stress axes. Measurements of flux rotation are therefore useful if the principal stress directions are unknown. The values of flux linkage and flux leakage also vary sinusoidally with probe orientation (in antiphase with each other), and the values are observed at the principal stress directions. If the principal stress directions are already known, then the probe 12 might instead be merely oriented to those directions, and the measurements made; no rotation of the probe 12 would be necessary.

Figure 3:
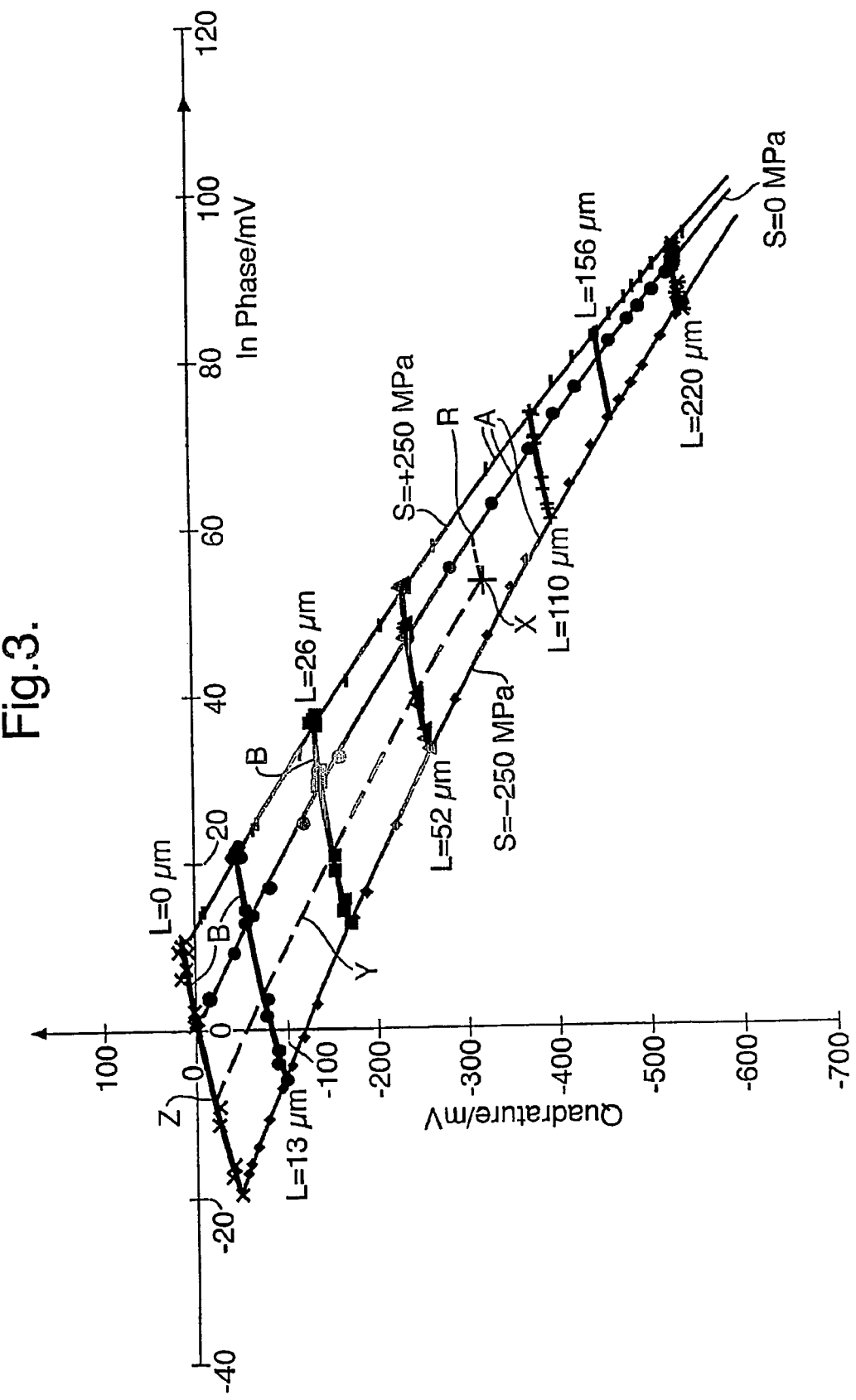
FIG. 3 shows graphically the variation of the backed-off quadrature and in-phase components of flux linkage with variations of lift-off, and with variations of stress.

The values of the stresses in the web in the vertical (i.e. perpendicular to the longitudinal axis) and longitudinal directions can be determined from the experimental measurements of flux linkage with the probe 12 oriented in those directions. This requires calibration of the apparatus 10, taking measurements on a sample of material of the same type as that of the rail 16, while subjecting it to a variety of different stresses. This may be done with a rectangular strip sample in a test rig, flux linkage measurements being made at the centre of the sample where the principal stress direction is aligned with the axis of the test rig. Referring to FIG. 3 this shows the backed-off flux-linkage in-phase and quadrature components obtained in such a test rig, the measurements being made with a drive frequency of 70 Hz, and the specimen being a steel bar. A first set of measurements were made at progressively larger values of lift-off, L, but with no stress, S. This gives the lift-off contour A, the lift-off varying between 0 and 220 microns. Similar lift-off contours A are obtained for other fixed values of stress, those for S=250 MPa tension and compression being shown. Measurements were then made at a range of different fixed values of lift-off, L, with varying stresses, S (both compression and tension), providing the contours B.

It will be appreciated that the contours A are curved, and the contours B are not orthogonal to the contours A, but that they intersect at substantially constant angles along any one lift-off contour A. Consequently it is only necessary to make calibration measurements sufficient to plot a few such contours A and B, and the shapes of the other contours can be predicted.

After calibrating the probe 12 in this manner, measurements of stress can be readily made from observations of flux linkage signals (resolved and backed off), as the contours enable the changes due to lift-off to be readily distinguished from changes due to stress. Any particular position in the impedance plane (i.e. in the graph of quadrature against in-phase components) corresponds to a particular value of stress and a particular value of lift-off. The mapping between (in-phase, quadrature) coordinates and (stress, lift-off) coordinates may be carried out graphically, referring to such contours, or by calculation. For example if the flux linkage signal has the in-phase and quadrature components of the position marked X, this corresponds to a lift-off of about 80 microns and a stress of about 125 MPa. Alternatively this value X may be translated (along the broken line Y) along a contour A of constant stress to find the in-phase and quadrature components at position Z that would be obtained with zero lift-off.

The value of stress found in this way is, it will be appreciated, the uniaxial stress that would provide that value of the flux linkage signal. If the stresses are actually biaxial, then a further calibration must be carried out with a cross-shaped sample in a test rig, flux linkage measurements being made at the centre of the sample where the principal stress directions are aligned with the axes of the test rig. Hence a graph or map may be obtained for a range of values of stress on one axis (say the x-axis) and for a range of values of stress in the other axis (say the y-axis), with contours each of which shows the values of biaxial stress that give a particular value of apparent uniaxial stress along the x-axis; and a similar graph may be obtained with contours showing values of biaxial stress that give a particular value of apparent uniaxial stress along the y-axis. Hence from measurements of apparent uniaxial stress along the two principal stress axes obtained as described earlier, the biaxial stress can be determined.

It will again be appreciated that the biaxial stress may be determined either graphically or by calculation in this way. Apparent values of uniaxial stress (in MPa) may be used for this purpose, or alternatively the numerical value of the flux linkage signal (in mV), either the in-phase or quadrature value, obtained by eliminating the effect of lift-off as described in relation to FIG. 3, may be used. Although the above method of correcting for lift-off has been described in relation to flux-linkage signals it is equally applicable to flux-leakage signals.

In the case of rail steels it has been found that the signals, if corrected for lift-off (for example as described above), both those for flux-linkage and those for flux-leakage, can be related almost linearly to the stress. (It will be appreciated that the flux-leakage signals increase as the flux-linkage signal decrease.) Measurements have been taken on nine different rails of different ages and from different manufacturers, on cut sections so that there is no thermally-induced stress; each section of rail was 3 m long or longer, and of the same grade of steel (220 grade) and cross-section (BS 113A). All the measurements were taken more than 0.3 m from either end to avoid those regions in which the residual stresses may have relaxed, and several different measurements were taken on each rail, along its length. There has been found to be a clear positive correlation between the signals in the longitudinal and vertical directions (i.e. parallel and perpendicular to the longitudinal axis), and so between the residual stresses in the longitudinal and vertical directions.

Figure 4:
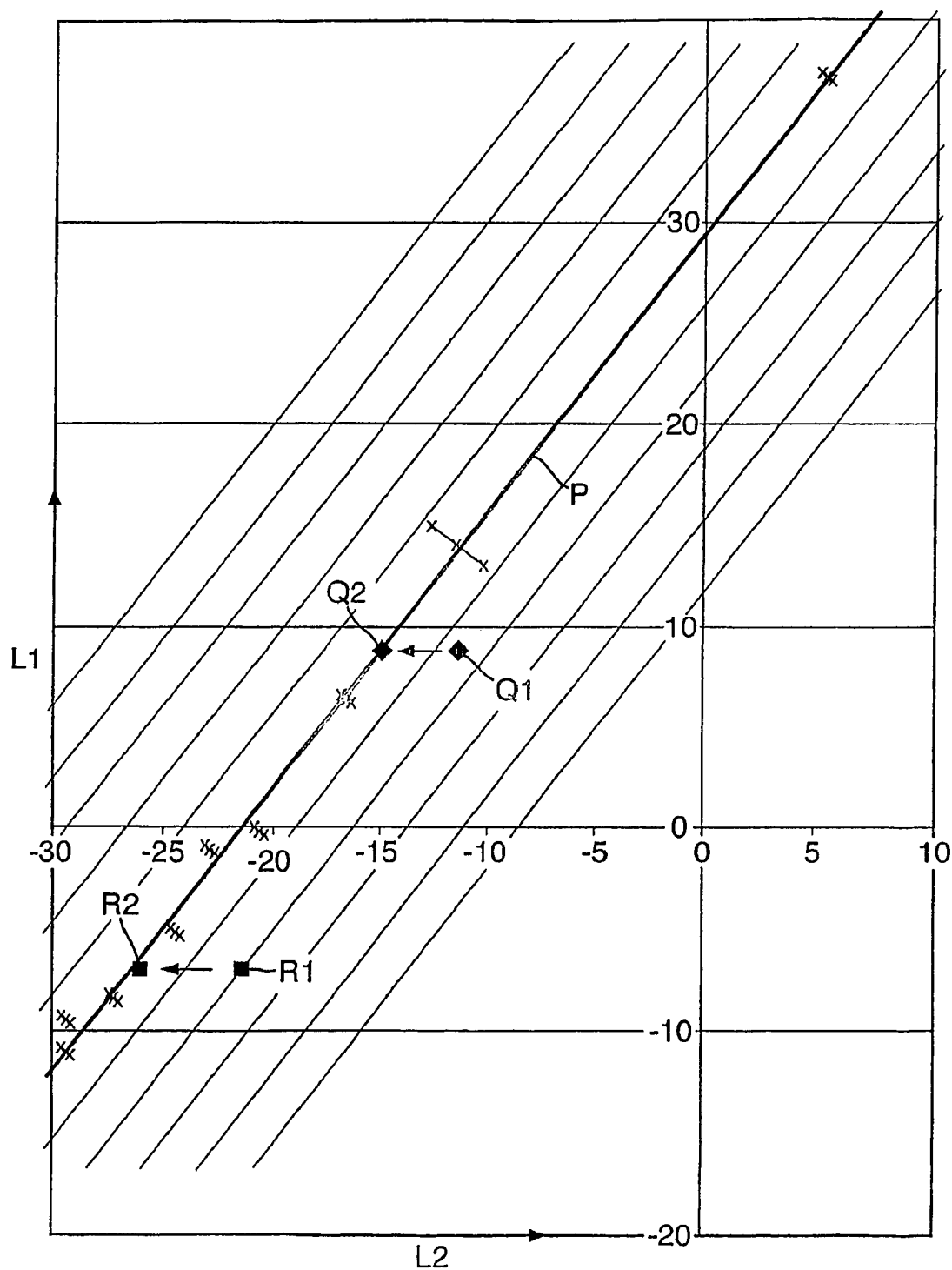
FIG. 4 shows graphically the correlation between the signals representing stress in the vertical and longitudinal directions in rail webs.

Referring now to FIG. 4, this shows graphically the flux linkage signal in the vertical direction (L1) and the flux linkage signal in the longitudinal direction (L2), each signal having been corrected for lift-off, the crosses showing the mean values for the measurements taken along each one of the nine different rail specimens, and the standard deviation of the discrepancies from the straight line P; the scatter along the straight line P is not indicated. (The numerical values on the axes are proportional to the signal voltages, 10 on the scale corresponding to 23 mV.) The positive correlation is clearly evident, and the straight line graph P may be represented by the equation:

$$L1=1.398L2+30.04$$

This experimentally-observed relationship between the vertical and longitudinal flux-linkage signals corresponds to a linear relationship between the vertical and longitudinal residual stresses. By measuring the stress in the vertical direction in a rail that is in situ (and in which there therefore may be thermally-induced stresses), this relationship enables the residual stress in the longitudinal direction to be determined. The difference between this and the observed total stress in the longitudinal direction consequently represents what is referred to as the thermally-induced stress.

The diamonds Q1, Q2 and the squares R1 and R2 on the graph show measurements made on a single rail in situ at different places along the rail after repeated cutting, re-stressing, and welding. The diamond Q1 shows the measurements on the rail before cutting, and Q2 shows the measurements after the rail has been cut. In this cut condition the rail is free standing, and there should therefore be no thermally-induced stress. As expected, Q2 lies very close to the straight line graph P. The square R1 shows the measurements at a different position on the same rail, after the rail has subsequently been restressed and welded, and R2 shows the measurements after the rail has again been cut. Once again, in the cut condition, one would expect there to be no thermally-induced stress; this is confirmed by the proximity of R2 to the straight line P.

It will thus be appreciated that from measurements such as Q1, the total longitudinal stress corresponds to the value L2=−11.6; without cutting the rail you can predict that the residual stress corresponds to the value L2=−15.3 (ie the L2 value on the line P at the same value of L1). Consequently the thermally-induced stress corresponds to the difference between these two values. The thermal stress can be expressed in terms of the stress-free temperature, for example by assuming that the longitudinal stress changes by 2.4 MPa/° C.; the faint lines parallel to the line P each represents a difference of 10° C. between the measurement temperature and the stress free temperature. For example, Q1 corresponds to a stress free temperature about 15° C. above the measurement temperature, while R1 corresponds to a stress free temperature about 20° C. above the measurement temperature.

Measurements of the stress free temperature made in this way can be compared to those measured using a strain gauge and cutting the rail. In one case, for example, measurements of the stress free temperature determined as described above gave results of 24° C. and 31° C., while the stress free temperature determined using the strain gauge and rail cutting gave results of 26° C. and 28° C.

The measurements taken above utilise flux linkage, but alternatively flux leakage signals could have been used.

The above signals were taken at 70 Hz, but alternatively the measurements might be made at a different frequency. In each case there will be a similar relationship between the vertical and longitudinal residual stresses. However, measurements at a higher frequency such as 500 Hz penetrate to a shallower depth into the rail, and this has been found to give a steeper straight line P, because the vertical stresses are greater nearer the surface. Any instability in the performance of the instrument tends to affect measurements of vertical and longitudinal stress equally, so the frequency is preferably selected to provide a straight line P whose gradient is 1.0; such instabilities would then move the measured point parallel to the line P, and so would not affect the accuracy of the measurement of stress free temperature.

In a further alternative, the residual longitudinal stresses may be correlated with the variation of vertical stress with depth. From measurements taken at several different frequencies, it is possible to deconvolve the measurements by assuming a functional form for the variation with depth (as described in US 2003/0071614A) and obtain values for the vertical stress at different depths. This can enable the exact variation of stress with depth to be determined. More simply, measurements might be taken at say two different frequencies, and the difference between those measurements correlated with the longitudinal stress measurements.

It will be appreciated that the present invention enables the stress-free temperature to be determined in a non-destructive fashion. It is applicable on both straight and curved tracks; it does not require the rail to be disconnected from the sleepers; and it is applicable whether the rail is under tension or compression.

The invention claimed is:

1. A method for determining the residual stress and the thermally-induced stress in a rail, the method comprising measuring the stresses in part of the rail remote from the railhead in a direction perpendicular to the longitudinal axis of the rail, and in a direction parallel to the longitudinal axis, determining from the stress in the perpendicular direction an estimate of the residual stress in the parallel direction, and hence by comparing the measured stress in the parallel direction to the estimated residual stress in the parallel direction determining the thermally-induced stress.

2. A method as claimed in claim 1 wherein the stresses are measured in the perpendicular and longitudinal directions in the web of the rail.

3. A method as claimed in claim 1 wherein the stresses are measured using an electromagnetic probe which comprises an electromagnet means comprising an electromagnetic core and two spaced apart electromagnetic poles, and at least one magnetic sensor arranged to sense either the reluctance of that part of the magnetic circuit between the poles of the electromagnet means, or flux-leakage between the poles of the electromagnet means.

4. A method as claimed in claim 1 wherein the residual stress in the longitudinal direction is determined from a correlation between it and the stress in the perpendicular direction.

5. A method as claimed in claim 1 wherein the residual stress in the longitudinal direction is determined from a correlation between it and the variation with depth of the stress in the perpendicular direction.

6. A method as claimed in claim 4 wherein the stresses are measured using an electromagnetic probe generating an alternating magnetic field, the frequency of the alternating magnetic field being selected such that the correlation between residual longitudinal stress and perpendicular stress can be represented by a straight line graph of gradient 1.

7. A method as claimed in claim 5 wherein the stressed are measured using an electromagnetic probe generating an alternating magnetic field, and the variation with depth of the stress in the perpendicular direction is determined from measurements at two different frequencies of the alternating magnetic field.

8. A method as claimed in claim 5 wherein the stresses are measured using an electromagnetic probe generating an alternating magnetic field, and the variation with depth of the stress in the perpendicular direction is determined by deconvolving measurements made at several different frequencies of the alternating magnetic field.

* * * * *